(12) United States Patent
Lehr et al.

(10) Patent No.: US 8,969,615 B2
(45) Date of Patent: Mar. 3, 2015

(54) PROCESS FOR PREPARING ISOCYANATES

(75) Inventors: Vanessa Simone Lehr, Mannheim (DE);
Torsten Mattke, Freinsheim (DE);
Carsten Knösche, Niederkirchen (DE);
Heiner Schelling, Kirchheim (DE);
Gerhard Olbert, Dossenheim (DE)

(73) Assignee: BASF SE, Ludwigshafen (DE)

( * ) Notice: Subject to any disclaimer, the term of this patent is extended or adjusted under 35 U.S.C. 154(b) by 139 days.

(21) Appl. No.: 13/434,135

(22) Filed: Mar. 29, 2012

(65) Prior Publication Data

US 2012/0251435 A1    Oct. 4, 2012

Related U.S. Application Data

(60) Provisional application No. 61/469,825, filed on Mar. 31, 2011.

(51) Int. Cl.
*C07C 263/00* (2006.01)
*C01B 7/04* (2006.01)
*C07C 263/10* (2006.01)

(52) U.S. Cl.
CPC ............... *C01B 7/04* (2013.01); *C07C 263/10* (2013.01)
USPC .......................................................... 560/347

(58) Field of Classification Search
CPC combination set(s) only.
See application file for complete search history.

(56) References Cited

U.S. PATENT DOCUMENTS

| | | | | |
|---|---|---|---|---|
| 4,231,959 | A * | 11/1980 | Obrecht | 562/847 |
| 7,442,935 | B2 | 10/2008 | Manneschi | |
| 2007/0043233 | A1 * | 2/2007 | Sanders et al. | 560/347 |
| 2007/0276154 | A1 * | 11/2007 | Haas et al. | 560/347 |
| 2011/0213177 | A1 | 9/2011 | Mattke et al. | |
| 2011/0230676 | A1 | 9/2011 | Lehr et al. | |
| 2012/0004445 | A1 | 1/2012 | Lehr et al. | |
| 2012/0046497 | A1 | 2/2012 | Stroefer et al. | |
| 2012/0095255 | A1 | 4/2012 | Mattke et al. | |
| 2012/0123152 | A1 | 5/2012 | Bruns et al. | |

FOREIGN PATENT DOCUMENTS

| | | |
|---|---|---|
| DE | 10 2006 024 549 A1 | 11/2007 |
| DE | 10 2009 032 413 A1 | 1/2011 |
| WO | WO 2010/115908 A2 | 10/2010 |
| WO | WO 2010/121997 A1 | 10/2010 |
| WO | WO 2010/149544 A2 | 12/2010 |
| WO | WO 2011/006970 A1 | 1/2011 |
| WO | WO 2011/018443 A2 | 2/2011 |
| WO | WO 2011/023638 A1 | 3/2011 |
| WO | WO 2011/036062 A2 | 3/2011 |
| WO | WO 2011/067369 A1 | 6/2011 |
| WO | WO 2011/104264 A1 | 9/2011 |
| WO | WO 2011/113737 A1 | 9/2011 |
| WO | WO 2012/049158 A1 | 4/2012 |
| WO | WO 2012/065927 A1 | 5/2012 |

OTHER PUBLICATIONS

U.S. Appl. No. 13/587,378, filed Aug. 16, 2012, Mattke, et al.
U.S. Appl. No. 13/687,670, filed Nov. 28, 2012, Mattke, et al.
U.S. Appl. No. 13/389,955, filed Feb. 10, 2012, Mattke, et al.
U.S. Appl. No. 13/393,251, filed Feb. 29, 2012, Denissen, et al.
U.S. Appl. No. 13/513,595, filed Jun. 4, 2012, Mattke, et al.
U.S. Appl. 13/380,680, filed Dec. 23, 2011, Heiner Schelling, et al.
U.S. Appl. No. 13/383,549, filed Jan. 11, 2012, Heiner Schelling, et al.
U.S. Appl. No. 13/394,647, filed Mar. 7, 2012, Torsten Mattke, et al.
U.S. Appl. No. 13/299,039, filed Nov. 17, 2011, Michael Bock, et al.
U.S. Appl. No. 13/661,652, filed Oct. 26, 2012, Leschinski, et al.

* cited by examiner

*Primary Examiner* — Karl J Puttlitz
(74) *Attorney, Agent, or Firm* — Oblon, McClelland, Maier & Neustadt, L.L.P.

(57) ABSTRACT

The present invention relates to gas phase phosgenation of amines for preparation of isocyanates. In the present invention, phosgene is prepared by reacting chlorine with an excess of carbon monoxide in a gas phase. The obtained phosgene-containing reaction mixture is divided into two streams by a thermal and/or a membrane separating process. The first stream is a low-carbon monoxide stream of no more than 1% by weight of carbon monoxide, based on a total weight of the first stream. The second stream is a carbon monoxide-rich stream of more than 10% by weight of carbon monoxide, based on a total weight of the second stream. The first stream is used as the phosgene-containing reactant stream in the gas phase phosgenation of amines to prepare isocyanates. The second stream can be recycled into the phosgene synthesis.

6 Claims, No Drawings

PROCESS FOR PREPARING ISOCYANATES

This patent application claims the benefit of U.S. provisional patent application Ser. No. 61/469,825 filed on Mar. 31, 2011 incorporated in its entirety herein by reference.

The invention relates to a process for preparing isocyanates by reacting the corresponding amines with phosgene, optionally in the presence of an inert medium, in the gas phase, and to a use of the hydrogen chloride coproduct of the gas phase phosgenation.

Gas phase phosgenation for preparation of isocyanates has the advantages over liquid phase phosgenation that a higher selectivity, a lower holdup of toxic phosgene, a reduced energy and lower capital costs are required.

In gas phase phosgenation, an amine-containing reactant stream is mixed with a phosgene-containing reactant stream, each in the gaseous state, and the corresponding diisocyanates are formed with release of hydrogen chloride. The reactants have to be vaporized beforehand and superheated at temperatures above 300° C. This vaporization/superheating is effected essentially indirectly by means of electrical heating, by means of combustion gases or by means of high-pressure steam. There may possibly also be a secondary heat carrier medium as an intermediate measure. The provision of the energy, especially for vaporization, is very costly.

The phosgene used in the phosgenation of the amines to prepare isocyanates is generally synthesized immediately upstream of the phosgenation. This involves reacting carbon monoxide with chlorine with release of heat (reaction enthalpy 110 kJ/mol), which has to be removed since full conversion is no longer possible above 100° C. owing to the position of the reaction equilibrium, to give phosgene.

In the gas phase reaction for synthesis of phosgene, carbon monoxide is generally used in excess in order to prevent breakthrough of the chlorine, i.e. in order to obtain substantially chlorine-free phosgene.

The phosgenation of amines to give isocyanates gives rise to a hydrogen chloride-containing offgas as a coproduct, which is generally sent to a further use, though residues of carbon monoxide still present therein can have adverse effects.

Therefore, DE-A1 10 2006 024 549 proposes a coupled process for synthesis of organic isocyanates, which comprises the preparation of phosgene by reaction of carbon monoxide with chlorine, the reaction of the phosgene with organic amines to form the corresponding isocyanates and the removal of the organic isocyanates, and wherein the carbon monoxide is removed from the hydrogen chloride-containing offgas of the isocyanate synthesis by reaction with chlorine to form phosgene. The phosgene is removed and can optionally be recycled into an isocyanate synthesis. The hydrogen chloride-containing, carbon monoxide-depleted gas is preferably subjected to a hydrogen chloride oxidation (Deacon process). The process thus enables removal of carbon monoxide from the hydrogen chloride-containing offgases of the isocyanate synthesis, in order thus to remedy disadvantages caused, especially in a downstream Deacon process, and at the same time to supply the carbon monoxide to a use with maximum economic viability.

The document points out that, in gas phase phosgenation, carbon monoxide contents up to 5% can be attained, because there is generally no condensation of the phosgene and hence no removal of the unreacted carbon monoxide before the phosgenation in such processes.

In contrast, however, it has been found that the carbon monoxide present in the phosgene-containing feed stream, when the latter comes directly from the synthesis of carbon monoxide and chlorine, which has to be run with a stoichiometric carbon monoxide excess, leads to problems in the gas phase phosgenation: at temperatures above 300° C., the Boudouard equilibrium in which carbon monoxide disproportionates to carbon and carbon dioxide is almost completely to the side of $CO_2$. The carbon formed leads to apparatus fouling and can additionally catalyze the decomposition of phosgene to chlorine and carbon monoxide, which in turn decomposes according to the Boudouard equilibrium to form further carbon, which in turn catalyzes the decomposition of further phosgene.

It was therefore an object of the invention to provide a process for preparing isocyanates by phosgenating the corresponding amines in the gas phase, which does not have the above disadvantages.

The object is achieved by a process for preparing isocyanates by phosgenating the corresponding amines in the gas phase, which comprises dividing a phosgene-containing reaction mixture from the gas phase synthesis of carbon monoxide and chlorine to phosgene, which is run with a stoichiometric carbon monoxide excess over chlorine, by means of a thermal separating process and/or of a membrane separating process into two streams, specifically into a first, low-carbon monoxide stream comprising not more than 1% by weight of carbon monoxide, based on the total weight of the first, low-carbon monoxide stream, and into a second, carbon monoxide-rich stream comprising more than 10% by weight of carbon monoxide, based on the total weight of the second, carbon monoxide-rich stream, and using the first, low-carbon monoxide stream as a reactant stream in the phosgenation of amines to isocyanates in the gas phase.

It has been found that the front end removal of the carbon monoxide from the phosgene-containing reaction mixture of the synthesis of carbon monoxide and chlorine before the phosgenation of the amines to give the corresponding isocyanates is a particularly advantageous separation step because it is very selective.

According to the invention, by means of a thermal separating process or of a membrane separating process from the phosgene-containing reaction mixture of the gas phase synthesis of carbon monoxide and chlorine to give phosgene, a first, low-carbon monoxide stream is removed, which comprises not more than 1% by weight of carbon monoxide, based on the total weight of the first, low-carbon monoxide stream.

Preferably, in the front end removal, the carbon monoxide content is lowered to not more than 1% by weight of carbon monoxide, based on the total weight of the first, low-carbon monoxide stream.

The gas phase synthesis of carbon monoxide and chlorine to give phosgene is preferably performed with a stoichiometric excess of carbon monoxide to chlorine of 0.01 to 25%.

Advantageously, a one-stage thermal separating process can be used.

Additionally preferably, a two-stage thermal separating process can be used.

In a further preferred embodiment, a multistage thermal separating process can be used.

The one-, two- or multistage separating process can be selected from simple separation by partial condensation, a distillation, an adsorption and an absorption.

The thermal separating process can be coupled to a membrane separating process. In a further embodiment, the phosgene-containing reaction mixture from the gas phase synthesis of carbon monoxide and chlorine to give phosgene is separated by means of a membrane separating process.

Advantageously, the first, low-carbon monoxide stream is obtained in liquid form and then vaporized, and then used in a gas phase phosgenation of amines.

This process regime gives rise to further advantages:

Liquid phosgene can be brought to a higher pressure level in a simple manner by means of a pump. For instance, the phosgene-containing stream can be provided without a direct coupling of the pressure levels of the phosgene synthesis and the gas phase phosgenation process for the gas phase phosgenation. Thus, it is possible in principle to operate the phosgene vaporization, the phosgene superheating or the gas phase phosgenation at a higher pressure per se than the phosgene synthesis.

Particularly advantageously, the phosgene-containing, low-carbon monoxide stream can be vaporized using the heat of reaction from the gas phase synthesis of carbon monoxide and chlorine. The phosgene synthesis supplies a sufficient amount of energy that the phosgene can optionally also be superheated after the vaporization.

However, it is also possible in principle to provide any lacking energy for vaporization or superheating by electrical heating or steam heating.

The coupling of the phosgene synthesis and of the vaporization of the condensed phosgene for heating purposes may be direct, by passing the phosgene to be vaporized through the exterior of the phosgene reactor. This process regime has safety advantages over cooling of the phosgene reactor with the heat carrier, water, since no water can get into the phosgene reactor in the case of a leak. For the coupling of the phosgene synthesis and of the phosgene vaporization for heating purpose, it is also possible to use a secondary heat carrier, for example a heat carrier oil.

However, it is also possible, as described in U.S. Pat. No. 7,442,935, to use the waste heat of the phosgene synthesis first to raise steam and then to use the latter for vaporization of the phosgene.

Preferably, the first, low-carbon monoxide stream obtained by a one-, two- or multistage thermal separating process and/or a membrane separating process is vaporized to a pressure level at least 10 mbar lower compared to the one-, two- or multistage separating process and/or membrane separating process for separation of the phosgene-containing reaction mixture from the gas phase synthesis of carbon monoxide and chlorine.

When the phosgene is condensed at a higher pressure level compared to the pressure level at which the condensed phosgene is then decompressed, direct heat coupling is possible, which means that the heat of condensation is sufficient for revaporization of the phosgene, and hence optimal exploitation is possible. Additional energy needed for vaporization can, however, also be effected by known industrial energy provision.

Advantageously, the second, carbon monoxide-rich stream comprising more than 10% by weight of carbon monoxide, based on the total weight of the second, carbon monoxide-rich stream, can be recycled into the phosgene synthesis.

In a preferred embodiment, the thermal separating process is a partial condensation, and the heat released from the condensation is utilized for the vaporization of the first, low-carbon monoxide stream.

The invention also provides for the use of the hydrogen chloride obtained as a coproduct in an above-described process for use in an oxychlorination, in a Deacon process for preparation of chlorine or in an electrolysis.

By virtue of performance, in accordance with the invention, of a front end removal of carbon monoxide before the use of the phosgene-containing reactant stream in the phosgenation, the hydrogen chloride-containing secondary stream also comprises only very low proportions of carbon monoxide, such that it can be used advantageously as a reactant stream in the above processes.

The invention claimed is:

1. A process for preparing an isocyanate via a gas phase phosgenation of a corresponding amine, the process comprising:
    reacting carbon monoxide with chlorine with a stoichiometric carbon monoxide excess over chlorine in a gas phase, thereby obtaining a phosgene-comprising reaction mixture;
    dividing the phosgene-comprising reaction mixture into a low-carbon monoxide stream and a carbon monoxide-rich stream by at least one separating process of a thermal separating process and a membrane separating process, wherein
    the low-carbon monoxide stream comprises not more than 1% by weight of carbon monoxide, based on a total weight of the low-carbon monoxide stream, and
    the carbon monoxide-rich stream comprises more than 10% by weight of carbon monoxide, based on a total weight of the carbon monoxide-rich stream; and
    introducing the low-carbon monoxide stream as a phosgene-comprising reactant stream into the gas phase phosgenation of the corresponding amine, thereby obtaining the isocyanate and hydrogen chloride as a coproduct wherein the low-carbon monoxide stream is obtained in liquid form and is vaporized by either heat generated from said reacting, or heat released from a partial condensation of phosgene during said thermal separating process.

2. The process according to claim 1, wherein in said reacting, the stoichiometric excess of carbon monoxide to chlorine in the gas phase is 0.01 to 25% by weight.

3. The process according to claim 1, wherein the thermal separating process is performed in at least one stage and is a process selected from the group consisting of a partial condensation, a distillation, an adsorption and an absorption.

4. The process according to claim 1, wherein the low-carbon monoxide stream obtained by the at least one separating process performed in at least one stage is vaporized to a pressure level at least 10 mbar lower than pressure in the at least one separating process.

5. The process according to claim 1, wherein the carbon monoxide-rich stream is recycled into said reacting.

6. The process according to claim 1, wherein the coproduct hydrogen chloride is employed in an oxychlorination, in a Deacon process for preparation of chlorine or in an electrolysis.

\* \* \* \* \*